(12) United States Patent
Kumar et al.

(10) Patent No.: US 7,479,536 B1
(45) Date of Patent: Jan. 20, 2009

(54) CHIRAL, CHARGED PEPTIDE NUCLEIC ACID OLIGOMERS FROM CYCLIC MONOMERS

(75) Inventors: Vaijayanti A. Kumar, Pune (IN); Moneesha D'Costa, Pune (IN); Krishnarajanagar N. Ganesh, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 153 days.

(21) Appl. No.: 09/666,144

(22) Filed: Sep. 20, 2000

(51) Int. Cl.
*A61K 38/00* (2006.01)
*A61K 31/70* (2006.01)
*A61K 31/425* (2006.01)
*C07K 1/00* (2006.01)

(52) U.S. Cl. .................. 530/324; 530/350; 514/44; 514/373

(58) Field of Classification Search .................. 530/350, 530/324; 514/373, 44; 548/210; 536/23.5
See application file for complete search history.

(56) References Cited

U.S. PATENT DOCUMENTS 6,716,961 B2 * 4/2004 Lowe .................. 530/300

OTHER PUBLICATIONS

Ray et al. (FASEB J 2000, vol. 14, pp. 1041-1060).*

* cited by examiner

*Primary Examiner*—J. E Angell
(74) *Attorney, Agent, or Firm*—Venable LLP; Ann S. Hobbs

(57) ABSTRACT

A novel class of peptide nucleic acid compounds, which are positively charged, chiral analogs based on cyclic monomeric units, bind to complementary ssDNA, dsDNA and RNA strands with more affinity than the corresponding achiral, linear peptide nucleic acids, without compromising the binding sequence specificity and the compounds of this invention are more soluble in water than the standard peptide nucleic acids.

10 Claims, 13 Drawing Sheets

Figure 6
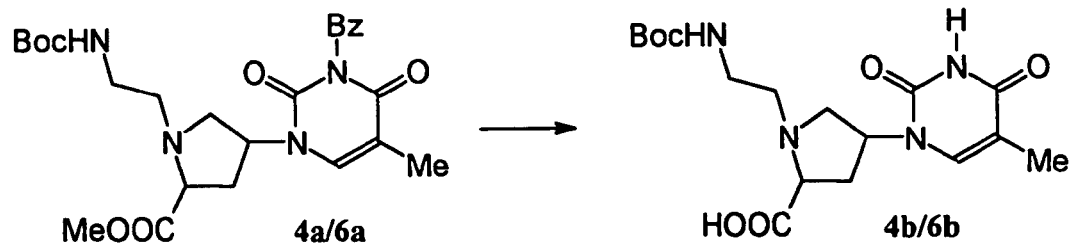
Figure 7  Solid Phase synthesis of Oligomers
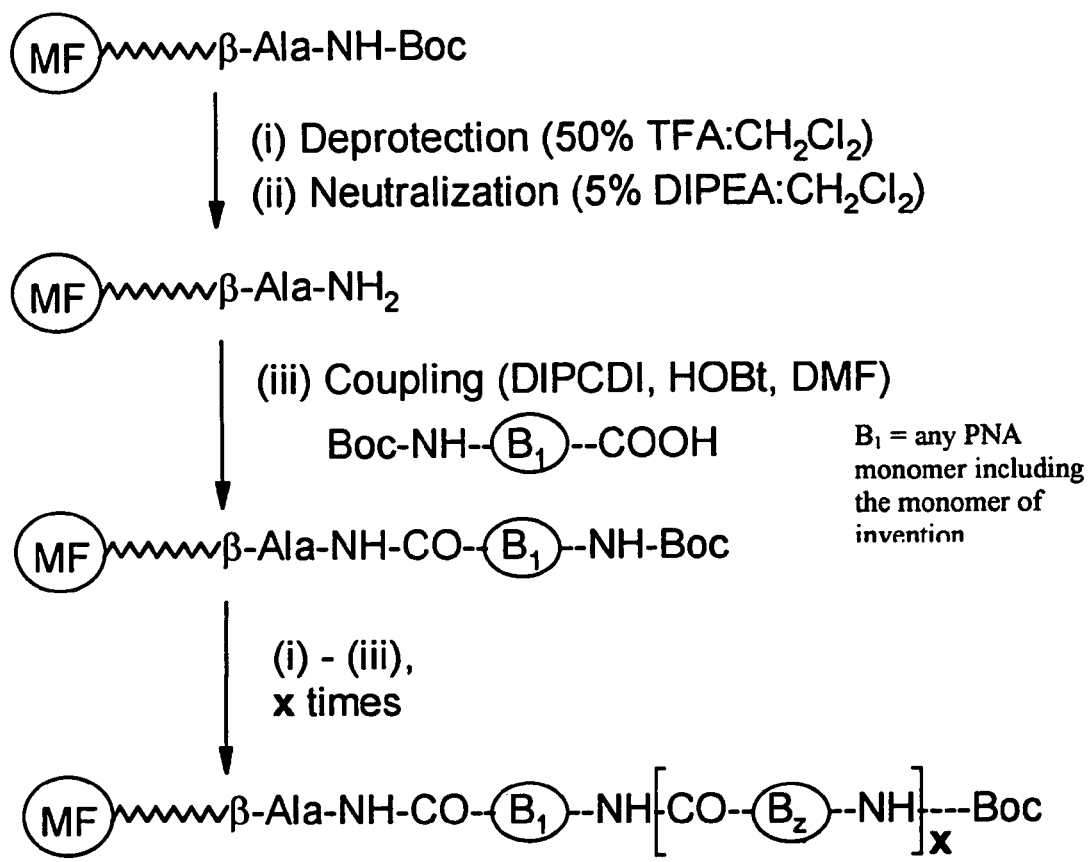

Figure 8. Oligomer sequences comprising novel monomers of the invention

Oligomer sequences

| 7 | H- T T T T T T t -(β-Ala)-OH |
| --- | --- |
| 8 | H- T T T t T T T t -(β-Ala)-OH |
| 9 | H- T t T t T t T t -(β-Ala)-OH |
| 10 | H- t t t t t t t -(β-Ala)-OH |
| 11 | H- T T T T T T T T -(β-Ala)-OH |
| 12 | H- t A T A T T A T T A T T -(β-Ala)-OH |
| 13 | H- T A T A T T A T T A T T -(β-Ala)-OH |

A/T = *aeg*PNA-A/T, t = *aep*PNA -T

DNA sequences

| 14 | 5'- G C A A A A A A A A C G -3' |
| --- | --- |
| 15 | 5'- G C A A A T A A A A C G -3' |
| 16 | 5'- A A T A A T A A T A T A - 3' |

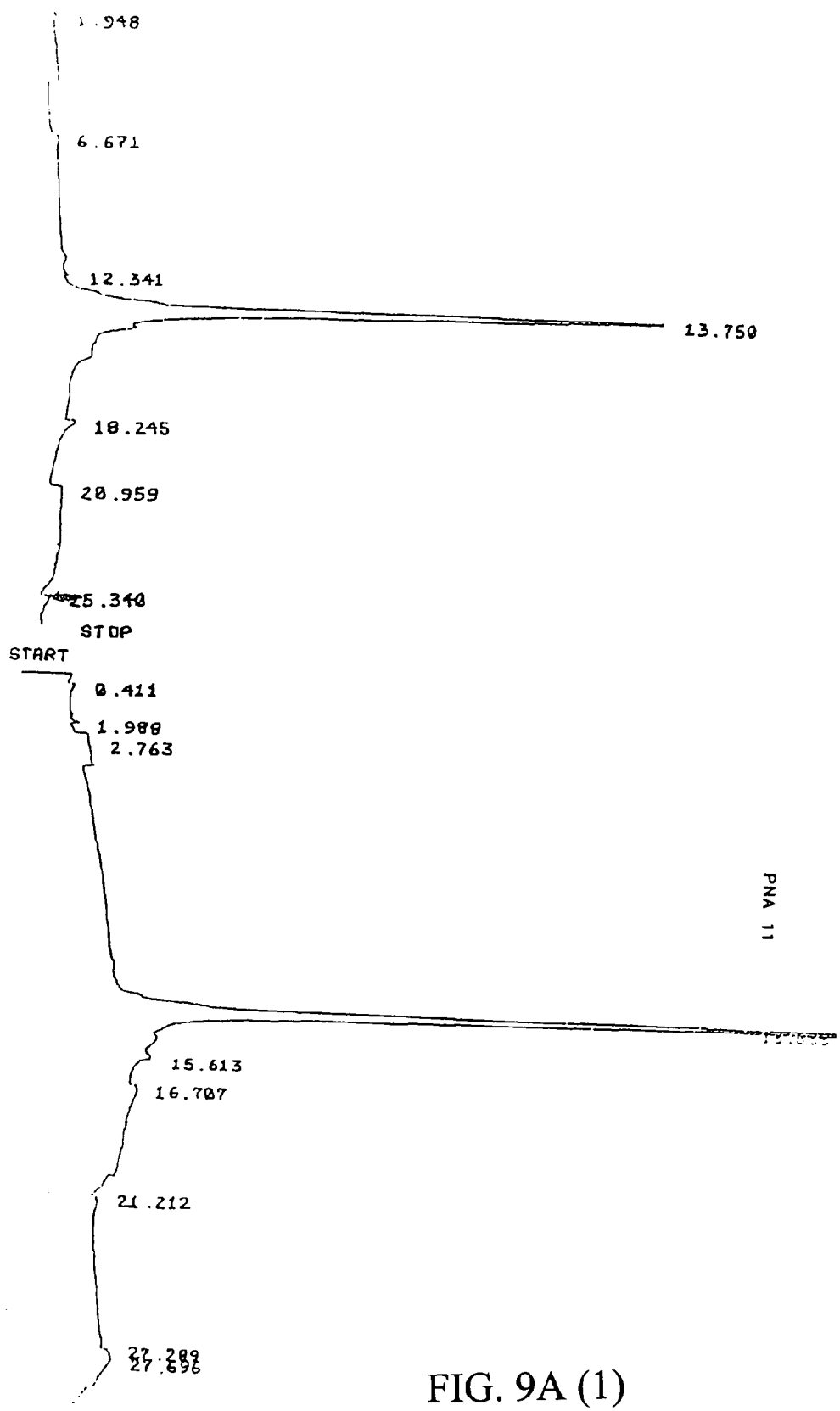
FIG. 9A (1)

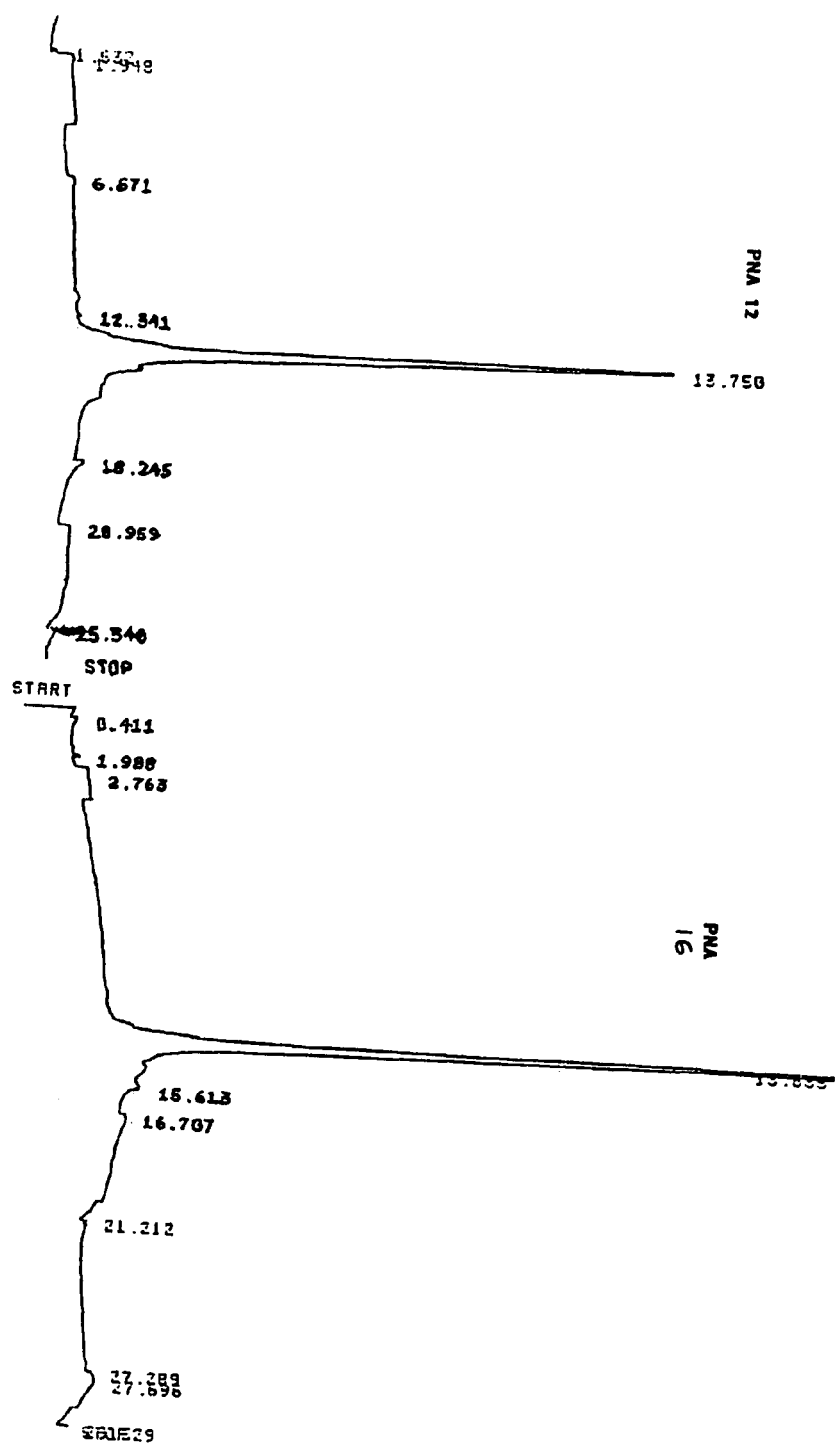
FIG. 9 A (2)

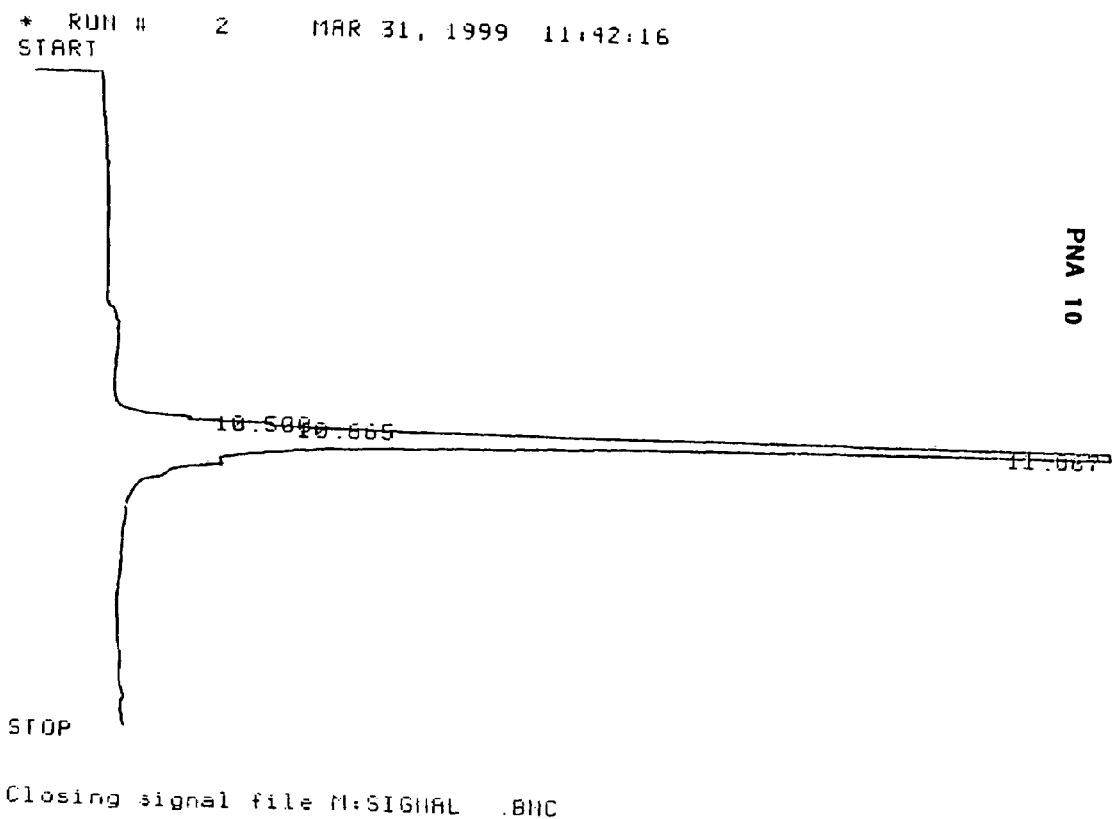
FIG. 9 B (1)

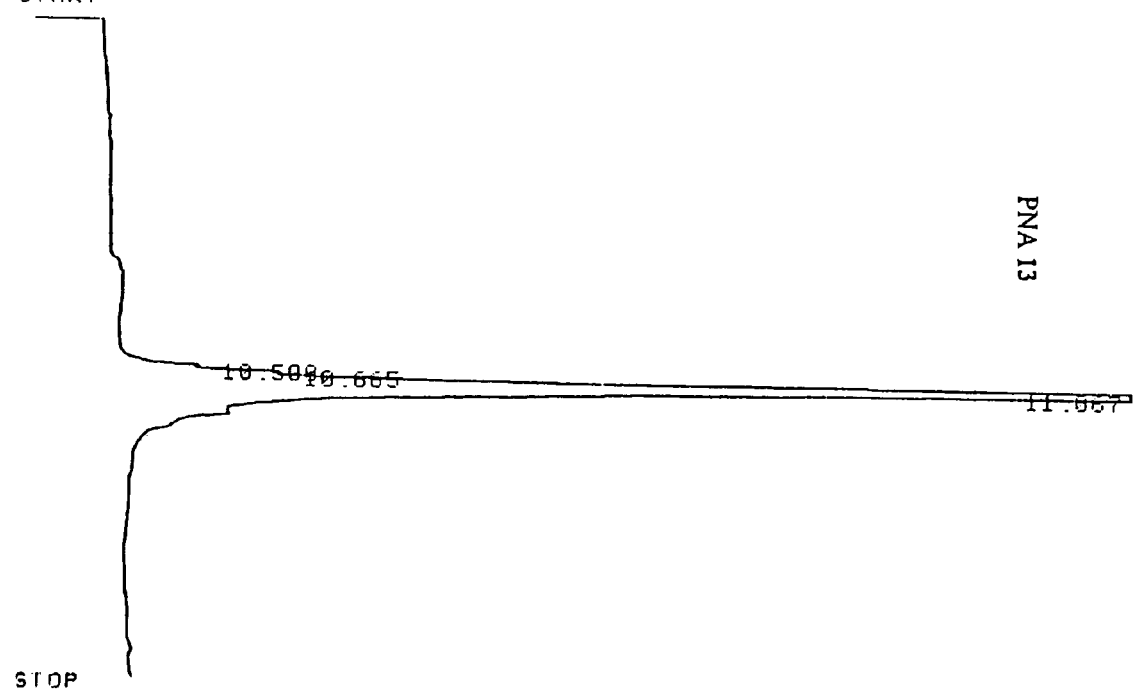
FIG. 9 B (2)

Figure 10:
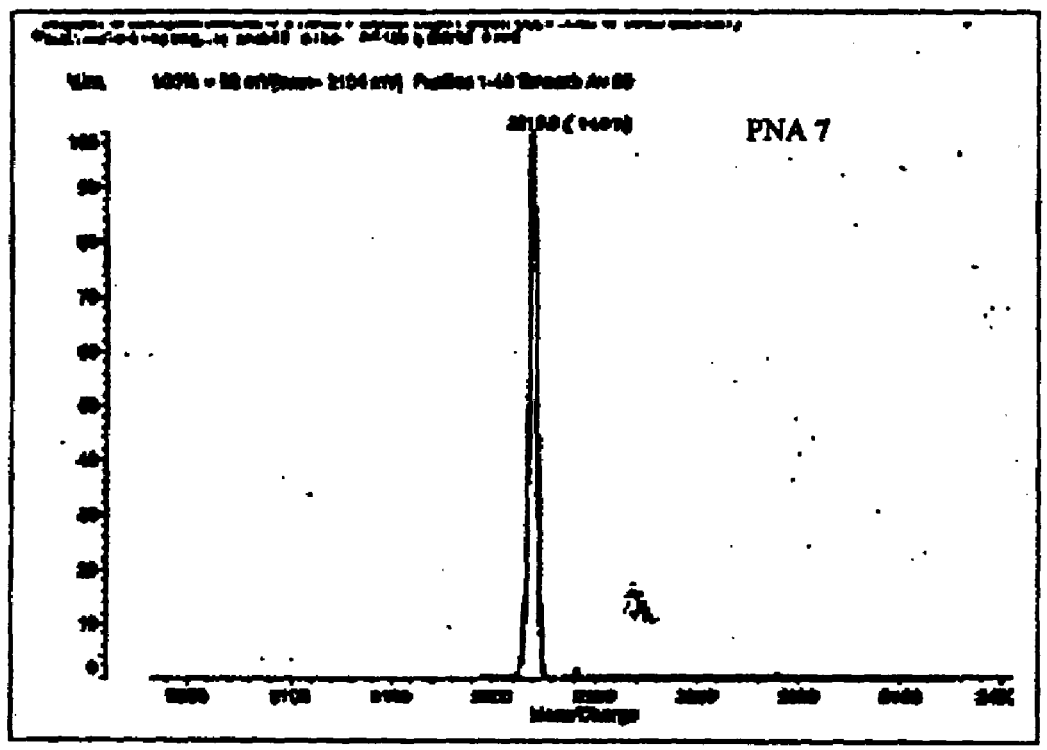
Figure 10:
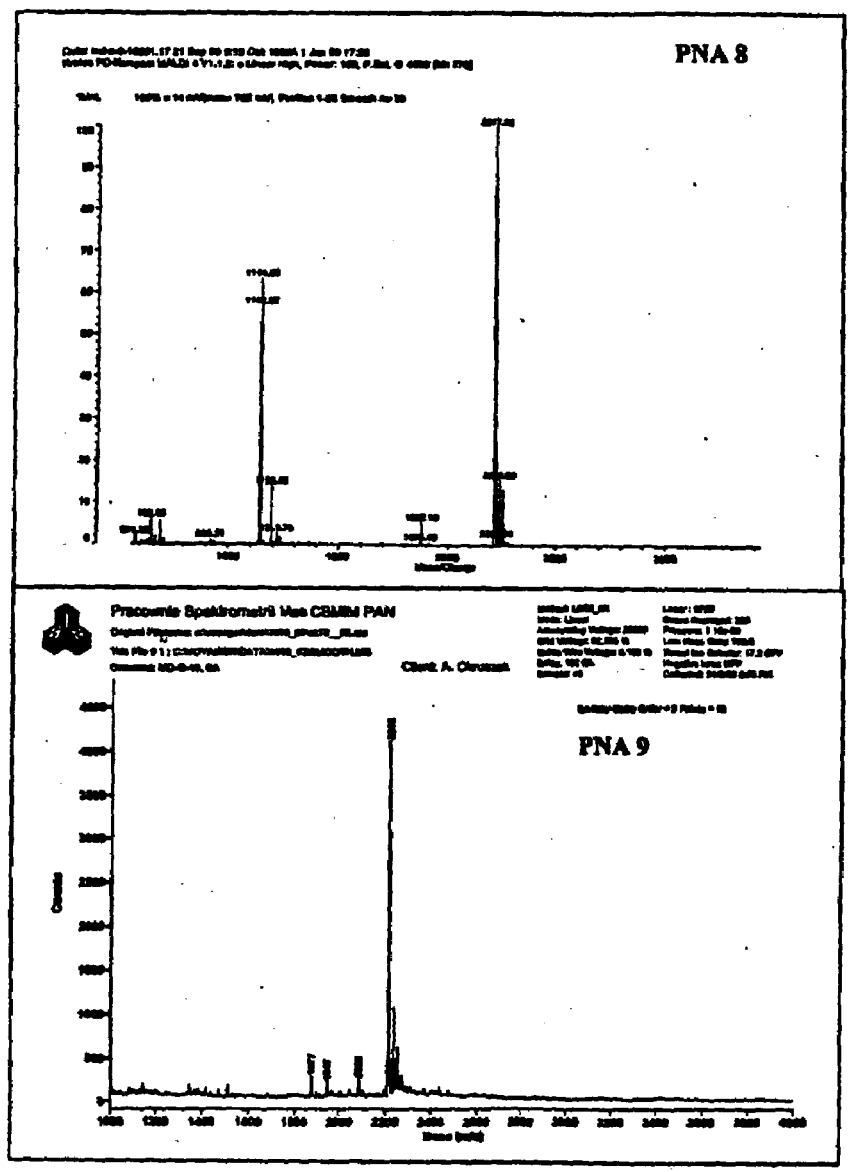
Figure 10:
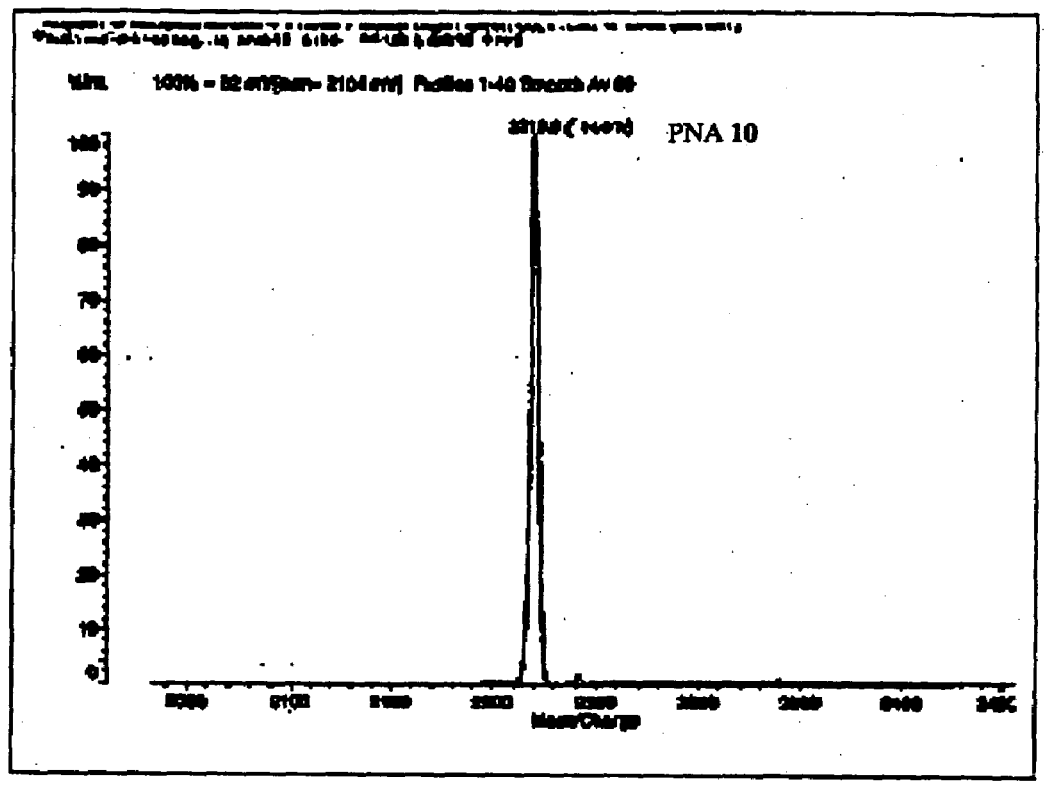

FIGURE 10 A. MALDI-TOF mass spectrum of PNA 10

Figure 10B. MALDI-TOF mass spectrum of PNA 11, 12
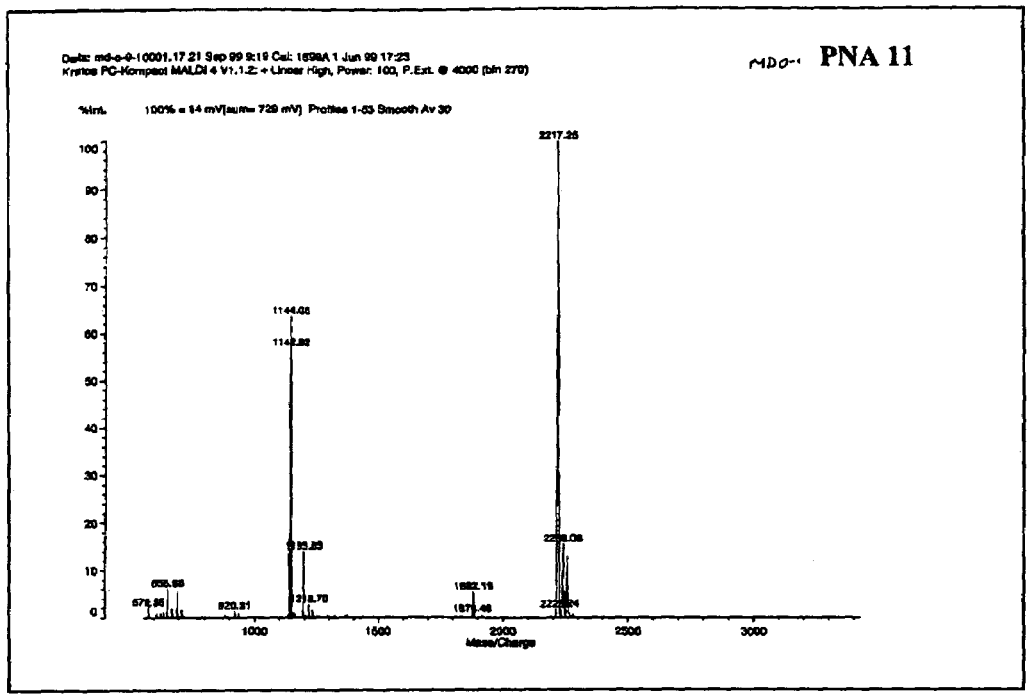
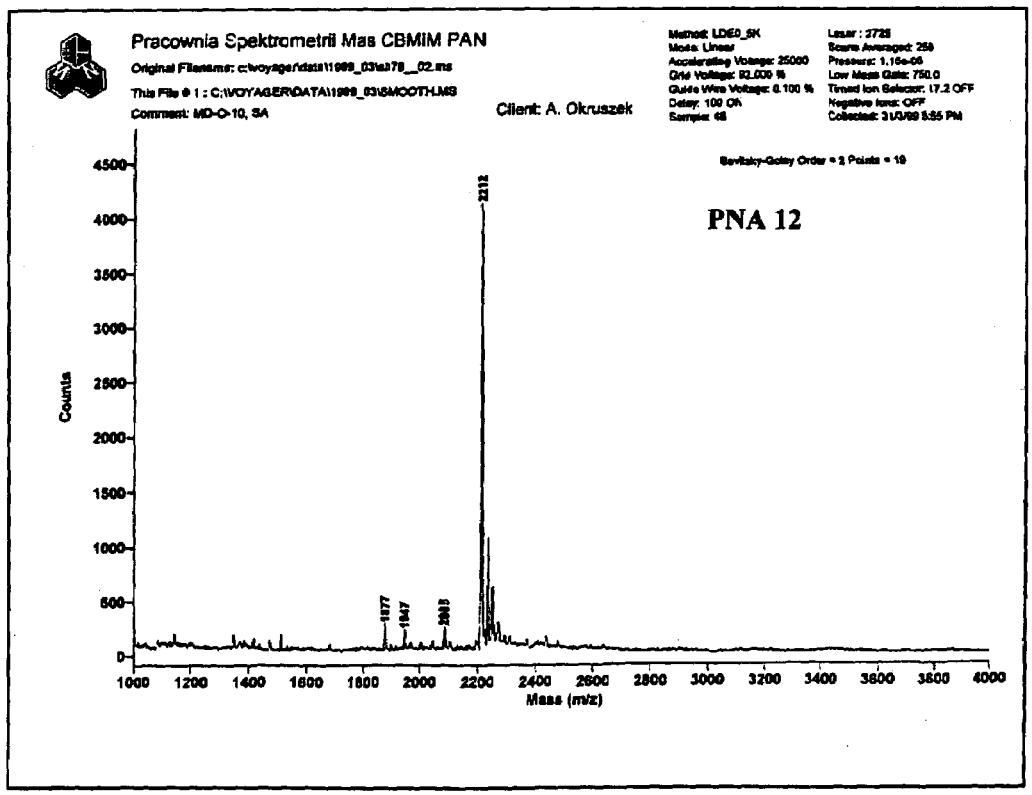
FIG.10 D UV melting profiles A: for the 2S modification a: 14:11, b: 14:7, c: 14:8, d: 14:9, e: 14:10.

B: a: 14:10, b: 15:10 and of single strands c: 15, d: 10.

FIGURE 12

Gel electrophoresis

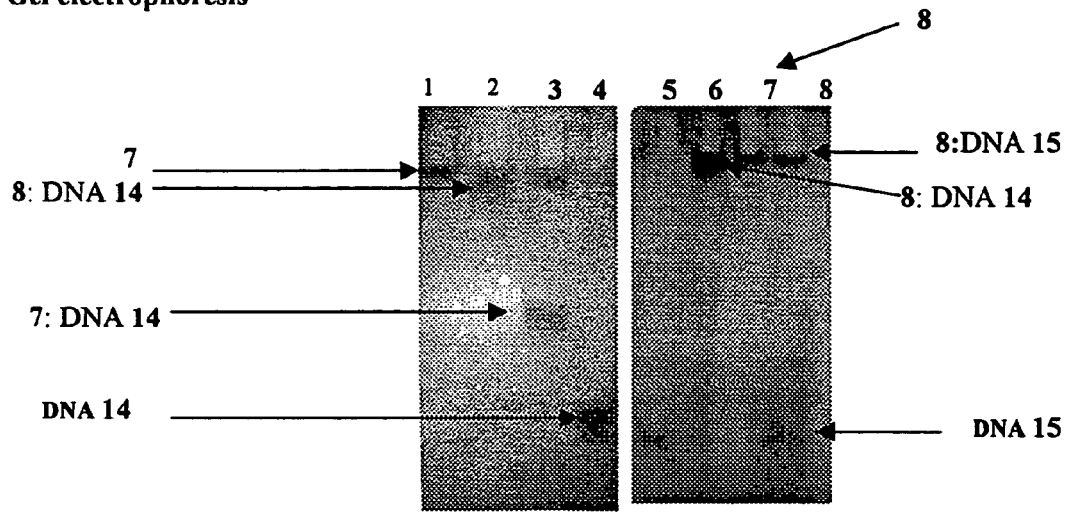

15% Polyacrylamide Gel Electrophoresis (acrylamide:*bis*-acrylamide, 29:1) of *aep*PNA:DNA complexes. Bands were visualized by UV-shadowing, i.e., by illuminating the gel placed on a fluorescent thin-layer silica gel chromatographic plate, $F_{254}$, 20cm x 20cm using UV light. Lane 1: 7; Lane 2: (8: DNA 14); Lane 3: (7: DNA 14); Lane 4: DNA 14; Lane 5: DNA 15; Lane 6: (8: DNA 14); Lane 7: 8; Lane 8: (8: DNA 15).

Oligomer sequences

7    H- T T T T T T T t -(β-Ala)-O⁻
8    H- T T T t T T T t -(β-Ala)-O⁻

T = *aeg*PNA-T, t = *aep*PNA -T

DNA sequences 14    5'- G C A A A A A A A C G -3'
15    5'- G C A A A T A A A A C G -3'

CHIRAL, CHARGED PEPTIDE NUCLEIC ACID OLIGOMERS FROM CYCLIC MONOMERS

FIELD OF THE INVENTION

This invention is related to novel compounds derived from peptide nucleic acids that bind to complementary DNA and RNA strands. In particular, the invention is concerned with peptide nucleic acid analogs that are chiral, positively charged, more soluble in aqueous systems and bind to complementary nucleic acid sequences with high avidity and sequence discrimination ability.

BACKGROUND OF THE INVENTION AND PRIOR ART

Gene targeted drugs are designed with oligonucleotides of nucleobase sequence of 10-20 units, complementary to the regulatory region of the disease associated target gene. Upon administration, they bind to specific promoter targets (DNA) and block access to RNA polymerase and as a consequence, no mRNA or the corresponding gene products are produced (Agarwal, S. in Applied antisense oligonucleotide technology, Stein, C. A. & Kreig, A. M. Ed., 1978, Wiley-Liss Inc). Depending on the target chosen, the drugs can be developed for application as antiviral, anticancer agents or other instances where conventional drugs have serious limitations. They are also useful for research and in diagnostics for detection and isolation of specific nucleic acids. Since natural oligonucleotides are degraded by nucleases, there is considerable interest in synthetic analogues of oligonucleotides that are stable under physiological conditions (Uhlmann, E. and Peyman, A. *Chem. Rev.* 1990, 90, 543; Leyten, I., Herdewijn, P., *Eur. J. Chem.*, 1998, 33, 515). In order to achieve this, a large number of variations in polynucleotide backbones have been undertaken, although so far not with the desired results. The great majority of these backbone modifications led to decreased stability for hybrids formed between the modified oligonucleotide and its complementary natural oligonucleotide, except in the case of aminoethylglycyl peptide nucleic acids (aegPNA I) (Nielsen, P. E. et al *Science* 1991, 254, 1497).

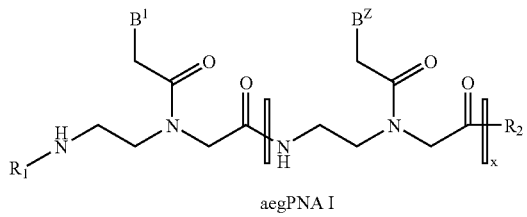

aegPNA I

In these compounds, a linear amide chain composed of repeating aminoethylglycine units to which nucleobase ligands are attached replaces the cyclic sugar-phosphate backbone of DNA and are amenable for easy preparation by solid phase peptide synthesis. PNAs can be used to target ss or ds DNA to produce gene regulatory molecules and as hybridization probes. Polypyrimidine PNAs form triple helices with ds DNA and are useful as antigene agents. Triplex formation and strand displacement are the only known principles in the art for sequence-specific recognition of ds DNA, with strand displacement being superior to the former. This is because unlike triplex formation, it is not restricted to homopurine-homopyrimidine sequences and allows the recognition of any sequence by Watson-Crick base pairing of the four natural nucleobases. The strand invasion of double strand DNA by unmodified PNAs is only possible in the absence of salts or at ionic strengths much lower than the physiological conditions. (Hyrup, B. and Nielsen P. E., *BioMed. Chem. Lett.* 1996, 4, 5).

The PNA molecules although make stable hybrids with complementary DNA, are poorly soluble in aqueous media and being non-chiral bind to complementary DNA in both parallel and antiparallel directions whenever the sequence permits (Hanvey, J. C. et al *Science* 1992, 258, 1481; Uhlmann, E. et al *Angew. Chem. Int. Ed Engl.* 1998, 37, 2796). Several structural variations within such a PNA backbone have been sought, in order to improve the water solubility, orientation specificity and DNA double strand invasion at physiological conditions, without compromising on the DNA affinity and sequence specificity. Typically, these involve conjugation with positively charged ligands such as lysine (Kim, S. H. et al *J. Am. Chem. Soc.* 1993, 115, 6477; Koch, T. et al *Tetrahedron Lett.* 1995, 36, 6933; Ishihara, T. and Corey, D. R. *J. Am. Chem. Soc.* 1999, 121, 2012) and introduction of substituents in the ethylenediamine or glycine sectors of the backbone. (Haaima, G. et al *Angew. Chem. Int. Ed. Engl.* 1996, 35, 1939; Gangamani, B. P. et al *Tetrahedron* 1999, 55, 177; D'Costa, M. et al *Organic Lett.* 1999, 1, 1513.). However, it is well understood in the art of the PNA backbone modifications that no PNA analogs have yet emerged where these problems have been simultaneously and satisfactorily addressed (Ganesh and Nielsen, *Curr. Organic Chemistry*, 2000, 9, 916). The following relevant patents on PNA so far are cited here.

| Patent No. | Authors | Title |
|---|---|---|
| 1 WO 9964449 | Harriot, P.; Nelson, J.; Wallace, A. | New cell permeable signal peptides useful for intracellular delivery of molecules |
| 2 WO 9816550 | Lowe, G. | New proline based chiral peptide nucleic acid compounds-having strong hybridisation activity, useful as antisense, antigene agents or in molecular biology |
| 3 WO 9714793 | Demidov, V. V.; Frank-Kamenetskii, M. D.; Veselkov, A. G. | Nucleic acid clamp comprising two sequences of peptide nucleic acids-connected by flexible linker with stabilizer at ends, used e.g., to cleave target nucleic acid |
| 4 WO 9620212 | Buchardt, O.; Lagriffoul, P.; Nielsen, P. E. | New peptide nucleic acid monomers with chiral backbone-may be used in preparation of oligomers useful e.g., as research tools |

OBJECTS OF THE INVENTION

It is the primary object of the present invention to provide novel cyclic, chiral PNAs—homo or hetero oligomers derived from the cyclic prolyl monomers that bind ssDNA and RNA strands to form stable hybrids with much higher affinity than the parent peptide nucleic acids.

It is one object of the present invention to provide cyclic monomers for peptide nucleic acid oligomers that bind single and double strand DNAs to form stable hybrids with higher affinity, than the corresponding complexes of the standard peptide nucleic acids I composed from linear monomer units with DNA.

It is another object of invention to provide monomers that are both cyclic and chiral for making oligomers that bind one strand of a double stranded polynucleotide, in a sequence and orientation specific manner.

It is yet another object of the invention to provide cyclic, chiral monomers that confer positive charge/s on the derived oligomers and make them more soluble in water than the standard peptide nucleic acids.

It is a further object to provide synthetic procedures for cyclic, chiral peptide nucleic acid monomers needed for the oligomers of the invention.

SUMMARY OF THE INVENTION

In summary, the invention provides novel entities viz., cyclic, chiral, positively charged oligomers that have specific advantages of higher solubility in water than standard PNA and bind to complementary DNA sequences in a sequence and orientation specific manner.

DETAILED DESCRIPTION OF THE INVENTION

The present invention provides a novel class of compounds (aepPNA II) incorporating cyclic monomers based on aminoethylprolyl (aepPNA) units that bind specifically to complementary ss and ds DNA and RNA strands. The compounds of the invention generally comprise ligands B (natural nucleobases thymine, cytosine, adenine or guanine, inosine, uracil and their synthetic analogs) linked to cyclic monomeric units that are an integral part of the peptide backbone. Further, the presence of two chiral carbon atoms (denoted by *) leads to four possible diastereomers and the compounds of the invention comprise all these stereomers.

In general embodiment, the oligomers of the invention are either homopolymers aepPNA II of the type

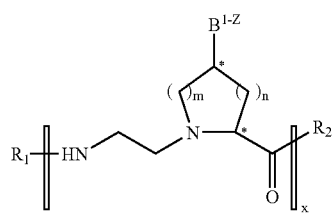

aep PNA II

Wherein m and n are 1 to 2 and x=1-20, each of $B^1$-$B^z$ is independently selected from the group consisting of H, HO, $NH_2$, naturally occurring nucleobases adenine (A), thymine (T), cytosine (C) and guanine (G), non-naturally occurring nucleobases, DNA intercalators, heterocyclic moieties and reporter ligands, each chiral monomeric unit independently selected from the four possible diastereomers, $R_1$=H/Fluorophore/Biotin, $R_2$=OH/NH$(CH_2)_2$COOH/NH $(CH_2)_3$NH$(CH_2)_4$NH$(CH_2)_3$NH$_2$.

Or heteropolymers aepPNA III involving one or more substitution of the aeg monomeric unit in the aepPNA II as below:

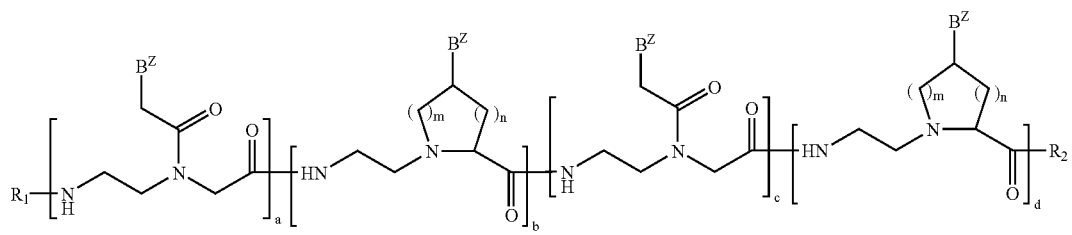

aep PNA III

Wherein
a, b, c, d, m, n are integers with values in the range 1 to 10 and various combinations thereof,
$R_1$ is $H_1COCH_3$ or L (corresponding to a fluorophore e.g. dansyl, carboxyfluorescein),
$R_2$ is OH, $NH_2$, NH $CH_2CH_2$COOH, sperminyl. i.e., NH$(CH_2)_3$NH$(CH_2)_4$NH$(CH_2)_3$NH$_2$.

In the following preferred embodiments, the compounds of the invention have m=n=1; $B^z$=T; $R_1$=H; $R_2$=NH$(CH_2)_2$ COOH, with (i) a=7, b=1, c=d=0, (ii) a=c=3, b=d=1, (iii) a=b=c=d=1, repeating twice in that order, (iv) a=b=c=0, d=8, and (v) a=d=0, b=1, c=7-11 and with various combinations of $B^z$.

The oligomers of the invention are synthesized by adaptation of standard peptide synthesis procedures, either in solution or in solid phase. The preferred monomer precursor-synthon, according to the invention, has the structure IV

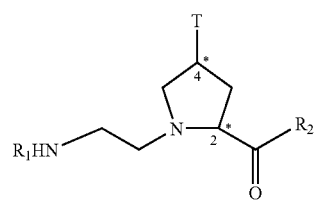

Where $R_1$=H/tBoc, $R_2$=Ome/OH at positions at 2 and 4 lead to four diastereomers, each synthesized by the process described in the invention (scheme 1) depending upon the stereochemistry of the starting material.

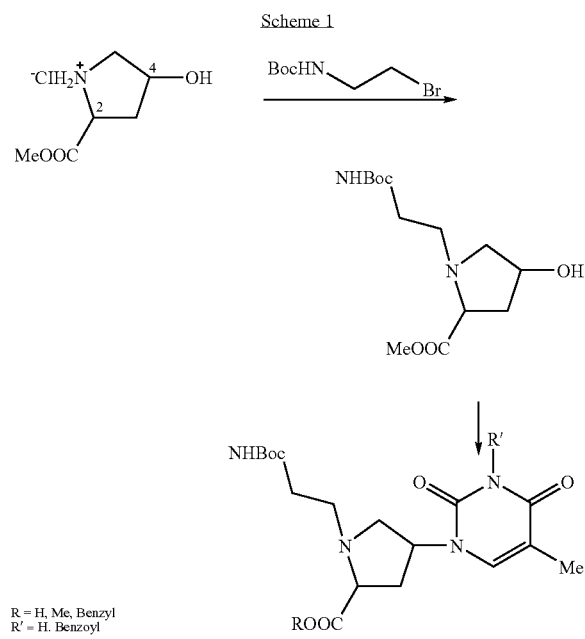

In all the monomer synthons and peptide nucleic acid analogs, according to the invention, the nucleobase is T. In alternative structures, B may be a non-naturally occurring nucleobase (nucleobase analog), another base-binding moiety, an aromatic moiety, hydroxyl or even hydrogen. The homooligomers aepPNA II, each incorporating the above monomers at all positions or heteropolymers aepPNA III, with inclusion of standard peptide nucleic acid monomers in the aepPNA II at one or more sites, are able to recognize the complementary polypurine, single stranded DNA, generating aepPNA:DNA complexes. Such a recognition of DNA taking place in the range of 8-15 bases is of biological interest.

While the oligomeric compounds of the invention show remarkably enhanced binding with complementary DNA as indicated by the increased Tm of hybrids, they also have significant discriminating ability as the presence of even a single mismatch in the complementary DNA strand would lead to significant destabilization of the complex. The present oligomeric compounds of the invention aepPNA II and aepPNA III are also more soluble in water than standard PNA I, making them more suitable for biological applications.

Whereas the improved binding of the compounds of the invention should render them efficient as antisense agents, it is expected that an extended range of related analogs or derivatives, whose structures are mentioned in the invention, may cause strand displacement. This should render them efficient antigene agents in inhibition of gene expression in cells.

BRIEF DESCRIPTION OF THE ACCOMPANYING DRAWINGS

Figure 1:
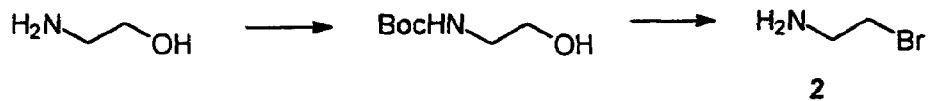

FIG. 1: Scheme for synthesis of (N-Boc)-2-aminoethylbromide

Figure 2:
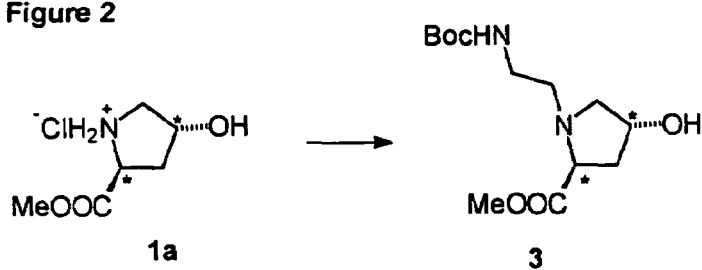

FIG. 2: Scheme for N-alkylation of 4R-hydroxy-2S-prolinemethylester

Figure 3:
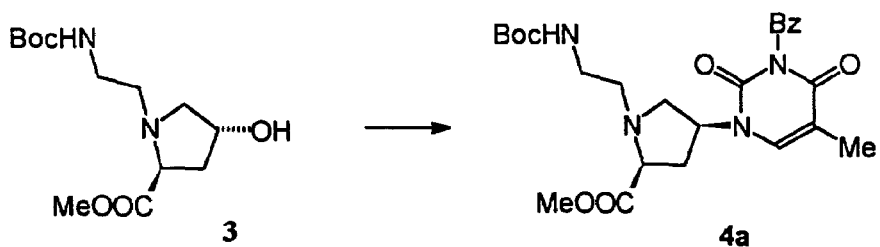
Figure 4:
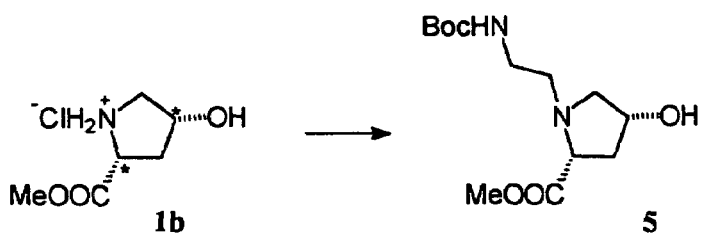
Figure 5:
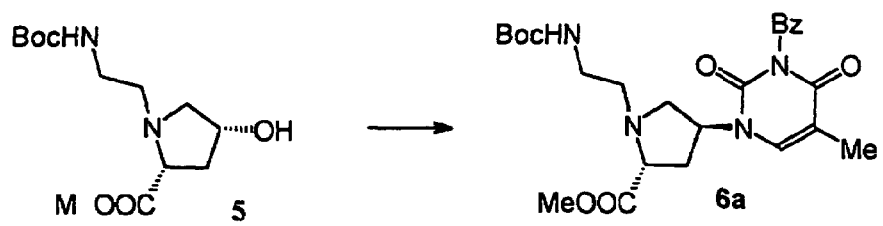

FIG. 3: Scheme for the synthesis of [1-(N-Boc)-2-aminoethyl]-4S-(N3-Benzoylthymin-1-yl)-2S-prolinemethylester FIG. 4: Scheme for N-alkylation of 4R-hydroxy-2R-prolinemethylester FIG. 5: Scheme for the synthesis of [1-(N-Boc)-2-aminoethyl]-4S-(N3-Benzoylthymin-1-yl)-2R-prolinemethylester FIG. 6: General scheme for ester hydrolysis to obtain protected monomer units FIG. 7: General scheme for solid phase synthesis of oligomers showing preparation of linear unprotected polyamides carrying novel monomers of the invention FIG. 8: Oligomer sequences comprising the novel monomer of the invention; oligomer sequence numbers 12-16 are disclosed as SEQ ID NOS 1-5 respectively.

FIGS. 9A(1), 9A(2), 9B(1), 9B(2): Reverse phase HPLC of some new oligomers of the invention.

FIGS. 10A-10D: MALDA-TOF spectra of some new oligomers of the invention.

Figure 11:
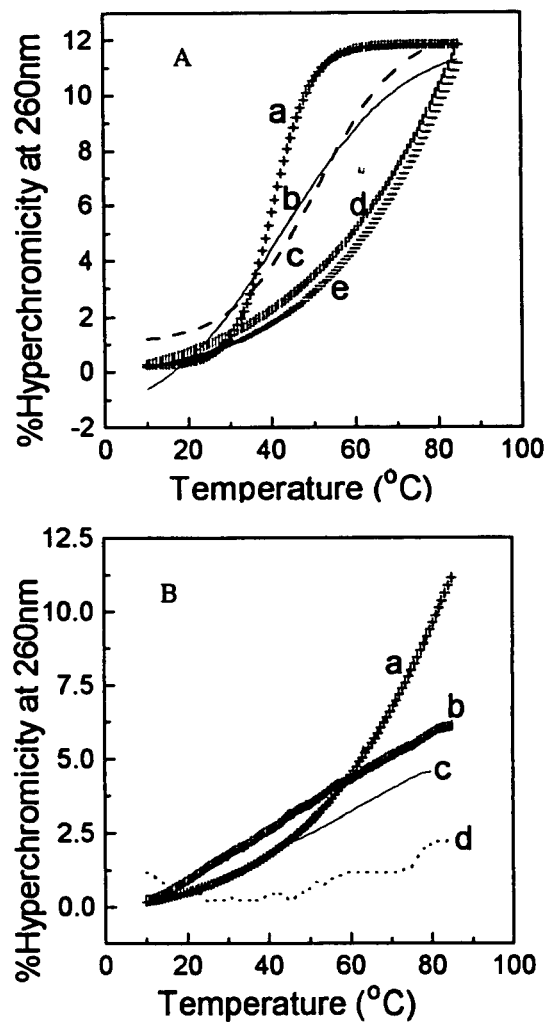

FIG. 11. UV melting profiles

FIG. 12: Gel electrophoresis; oligomer sequence numbers 14 & 15 are disclosed as SEQ ID NOS 3 & 4 respectively.

The peptide nucleic acids have been found to be superior to oligonucleotides since they have significantly higher affinity for complementary RNA or DNA. Since they are amides of non-biological amino acids, they are biostable and resistant to enzymatic degradation by proteases and nucleases. However, their properties in terms of solubility, cellular uptake and specific orientation in hybridization are not satisfactory and need to be improved by novel approaches.

The main descript of the invention is the structural design which simultaneously installs positive charges and chirality on the main backbone accompanied by controlled conformational restriction as a strategy to overcome the many limitations of peptide nucleic acids. This is achieved by linking of the α-carbon of glycyl component with the β-carbon of the side arm carrying the ligand B in peptide nucleic acids I to obtain the monomer synthons IV. The compounds of the invention, the size of the cyclic system are determined by independent values for m and n, which vary between 1 and 2. In the preferred synthons of the invention, m=n=1, correspond to aminoethylprolyl PNA aepPNA (II). An important consequence of such a structural design is the presence of a tertiary amino group in the oligomer of the invention, which has a potential for protonation at physiological pH, leading to positively charged oligomers that have better hybridization properties with the negatively charged complementary DNA and improved solubility in aqueous systems.

In another interesting aspect of the invention, chirality is introduced at 2 centers in the cyclic pyrrolidine ring system, resulting in 4 diastereomeric monomers. The polymeric oligomers of the invention are derived from these chiral monomers, leading to stereoregular (homochiral) or stereo-alternating polymers (heterochiral). Such stereocontrolled and stereodefined oligomers derived from the chiral monomers of the invention can be used to influence the strand orientations of PNA in PNA:DNA complexes and have benefits in terms of unambiguous, orientation dependent complementary recognition of DNA by the oligomers of the invention.

In a further aspect of the invention, a novel process for the synthesis of the monomers is described (Scheme 1). The route consists of 2 steps starting from 4-hydroxyprolinemethylester hydrochloride and involves N-alkylation, followed by a Mitsunobu reaction. The invention also comprises a process for making the (N-Boc)-2-aminoethyl bromide, which is the alkylating agent. The process described in the invention is also applicable for the synthesis of the other diastereomers, depending on the stereochemistry of the starting material.

It is observed that oligomers of the present invention overcome some of the biochemical/biophysical limitations of peptide nucleic acids I such as low solubility in water and relative orientations of strands in duplex and triplex structures. The oligomers of the invention are synthesized by a methodology similar to that of PNA, in which the monomer synthons are coupled either to the standard PNA monomer or another modified monomer of the invention. This is useful in adaptation of the present synthetic set-ups for the synthesis of oligomers of the invention.

General Method for the Synthesis of Monomers

One monomer synthon, according to the invention, is prepared by N-alkylation of 4R-hydroxy-2S-prolinemethyl ester 1 with (N-Boc)-2-aminoethylbromide 2 to afford [1-(N-Boc)-2-aminoethyl]-4R-hydroxy-2S-proline derivative 3 (FIG. 2). The alkylating agent 2 was prepared in two steps from 2-aminoethanol by first making its NH-Boc derivative followed by bromination (FIG. 1). The C4 hydroxyl function in 3 was replaced with N3-benzoylthymine using Mitsunobu reaction to yield the (2S,4S) ester 4a (FIG. 3). Similarly, N-alkylation of 4R-hydroxy-2R-prolinemethylester 5 (FIG. 4), followed by Mitsunobu reaction with N3-benzoylthymine (FIG. 5) gave the (2R,4S)-ester 6a. The (2R,4S) 6a and (2S, 4S) 4a esters were hydrolyzed (FIG. 6) to provide the cyclic monomers 4b and 6b for the oligomer assembly.

Additional objects, advantages and novel features of the cyclic monomers, and the process invention will become apparent to those skilled in the art of synthesis for e.g., the 4-hydroxy groups in the starting prolinemethylesters can be inverted by Mitsunobu reaction to obtain the other two diastereomers. Other features of the invention are illustrated by the following examples thereof, which are not intended to be limiting.

General Method for Synthesis of Oligomers of the Invention

Oligomers of the invention were prepared generally in accordance with the currently practiced art using solid phase synthesis (FIG. 7). Merrifield resin derivatized with N-Boc-β-alanine (0.13 meq/g of resin) was treated with a three-fold excess of a monomer to be coupled in DMF, along with the coupling agents, diisopropylcarbodiimide and HOBt, (0.4 meq each/g resin) in DMF (2 ml/g resin). The removal of the Boc protecting group in the product is accomplished by trifluoroacetic acid treatment and the efficiency of the deprotection and the coupling reactions were determined by the Kaiser test. After sequential addition of monomers, the product oligomer comprising the monomers of the invention was released from the resin by treatment with trifluoroacetic acid-trifluoromethane sulphonic acid. The products were purified using FPLC, their purity checked by HPLC (FIG. 9) with acetonitrile-water (0.1% TFA) gradient and their molecular composition confirmed by MALDI-TOF mass spectrometry (FIG. 10). The oligomer sequences synthesized by this method are listed in FIG. 8.

General Method for Evaluating the Stability of Hybrids of Compounds Under Invention with Complementary Polynucleotides The oligomers of the invention prepared as above were evaluated for their ability to hybridize with complementary oligonucleotides. This was done by monitoring the temperature dependent UV absorbance (260 nm) of stoichiometrically mixed solutions of PNA oligomers with that of specific sequences of oligodeoxyribonucleotides. The temperatures at the midpoint of the observed sigmoidal transitions (Tm) were taken as a measure of the stability of the PNA:DNA hybrids (FIG. 11, Table 1). When the stoichiometry of PNA:DNA is 2:1, the complexes are present: as triplexes. The absence of a well-defined transition was considered as evidence for unstable PNA:DNA complexes. The results indicated that the presence of even a single subunit of compounds of the invention II increased the stability of the derived hybrids as compared to the standard PNA of identical sequence (aegPNA I). An increase in the number of monomeric units of the invention further enhanced the stability of complexes to the extent that the homooligomeric PNA:DNA complex did not dissassociate even up to 80° C., indicating an extremely high stability. The presence of a single mismatch in the complementary oligonucleotide of PNA:DNA mixture led to very significant destabilization of the complex. The formation of complexes was also checked independently by gel electrophoresis experiments under non-denaturing conditions (FIG. 12) in which the successful complex formation is accompanied by a retardation in the electrophoretic mobility of the corresponding samples. Further, the oligomers or their complexes even with prolonged storage did not precipitate, unlike analogous standard PNA solutions, suggesting remarkably improved aqueous solubility of the oligomers of the invention. These results demonstrate the novel properties of the oligomers composed of the preferred monomers of the invention—namely enhancing the aqueous solubility and stability of the complexes with oligonucleotides, without compromising the sequence fidelity.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

TABLE 1

UV-$T_m$ (° C.) of DNA:PNA complexes*

| | DNA:PNA$_2$ | 2'S | 2'R |
|---|---|---|---|
| 1 | 14:7 | 44 | 42 (38) |
| 2 | 14:8 | 51 | 54 |
| 3 | 14:9 | >75 | >75 (67) |
| 4 | 14:10 | >80 | >80 (>74) |
| 5 | 15:9 | nd | nd |
| 6 | 15:10 | nd | nd |
| 7 | 14:11 | | 43(38) |
| | DNA:PNA | | |
| 8 | 16:12 | 41 | |
| 9 | 16:13 | | 39 |

*nd: not detected. Buffer: 10 mM sodium phosphate, pH 7.4. Values in brackets: $T_m$ (° C.) with 100 mM NaCl. $T_m$ values are accurate to (±)1° C. Experiments were repeated at least thrice and the $T_m$ values were obtained from the peaks in the first derivative plots.

Another embodiment of this invention provides a method of using peptide nucleic acid oligomers of the present invention for diagnosing and/or modulating the expression of genes in organisms. The modulation includes inhibiting transcription and replication of the said gene.

Yet another embodiment of the present invention provides a process for treating disease conditions associated with undesired protein production in an organism by using the novel compounds of the invention.

Still another embodiment of the present invention provides a pharmaceutical composition comprising a compound of the present invention along with any other pharmaceutically effective agents.

Additional objects, advantages and novel features of this invention will become apparent to those skilled in the art upon examination of the following examples thereof, which are not intended to be limiting.

EXAMPLE 1

Preparation of the Precursor (N-Boc)-2-Aminoethanol, Needed to Prepare the Alkylating Agent To a cooled, stirred solution of 2-aminoethanol (5.9 ml, 0.098 mol) and sodium hydroxide (3.6 g, 0.098 mol) in water-dioxane (1:1), was added drop-wise Boc-azide (10 ml, 0.081 mol). The reaction was stirred at room temperature overnight. The dioxane was then removed under vacuum, and the water layer extracted several times with ethyl acetate. The organic layer was dried over sodium sulphate and then, evaporated to dryness under vacuum to get the product (N-Boc)-2-aminoethanol (5.37 g, 41% yield), which was used in further steps without purification.

EXAMPLE 2

Preparation of the Alkylating Agent (N-Boc)-2-Aminoethylbromide 2 Required for the Synthesis of Compound 3

To an ice-cooled solution of (N-Boc)-2-aminoethanol (2.5 g, 15.5 mmol) and carbon tetrabromide (7.5 g, 22.7 mmol) in dry benzene (25 ml), was added triphenyl phosphine (4.7 g, 17.9 mmol) in small portions over 10-15 min. After 30 min. solvent was evaporated and the product immediately purified by silica gel column chromatography to get (N-Boc)-2-aminoethylbromide (5.53 g, 790%).

$^1$H NMR (CDCl$_3$) δ: 4.95 (br s, 1H, NH), 3.50 (m, 4H, (CH$_2$)$_2$), 1.45 (s, 9H, C(CH$_3$)$_3$)

EXAMPLE 3

Alkylation of 4(R)-hydroxy-2(S)-prolinemethylester 1a with 2 to Obtain Starting Material [1-(N-Boc)-2-aminoethyl]-4(R)-hydroxy-2(S)-prolinemethylester 3 for the Synthesis of Monomers of the Invention A mixture of 4(R)-hydroxy-2(S)-prolinemethylester hydrochloride (3.24 g, 17.9 mmol), (N-Boc)-2-aminoethylbromide (2.0 g, 8.9 mmol) and anhydrous potassium carbonate (3.69 g, 26.7 mmol) was stirred together in DMF:acetonitrile (1:1) at room temperature for 72 h under argon atmosphere. After completion of reaction as indicated by TLC, solvents were removed in vacuo. The residue was taken in water and extracted with ethyl acetate (4×30 ml). The organic layer was dried over sodium sulphate and concentrated to get the crude product, which was purified by silica gel column chromatography. The pure product was obtained in 56% yield.

$^1$H NMR (CDCl$_3$) δ: 5.30 (br s, 1H, NH), 4.40 (m, 1H, H4), 3.70 (s, 3H, OCH$_3$), 3.50 (t, 1H, H5), 3.38 (dd, 1H, H5'), 3.10 (dd, 2H, Boc-NH—CH$_2$), 2.70 (br m, 4H, H2, Boc-NH—CH$_2$—CH$_2$, OH), 2.50 (dd, 1H, H3), 2.10 (m, 1H, H3'), 1.40 (s, 9H, C(CH$_3$)$_3$)

EXAMPLE 4

Alkylation of 4(R)-hydroxy-2(R)-prolinemethylester 1b with 2 to Obtain Starting Material [1-(N-Boc)-2-aminoethyl]-4(R)-hydroxy-2(R)-prolinemethylester 5 for the Synthesis of Monomers of the Invention A mixture of 4(R)-hydroxy-2(R)-prolinemethylester hydrochloride (3.24 g, 17.9 mmol), (N-Boc)-2-aminoethylbromide (2.0 g, 8.9 mmol) and anhydrous potassium carbonate (3.69 g, 26.7 mmol) were stirred together in DMF:acetonitrile (1:1) at room temperature for 72 h under argon atmosphere. After completion of reaction as indicated by TLC, solvents were removed in vacuo. The residue was taken in water and extracted with ethyl acetate (4×30 ml). The organic layer was dried over sodium sulphate and concentrated to get the crude product, which was purified by silica gel column chromatography. The pure product was obtained in 56% yield from (N-Boc)-2-aminoethyl bromide.

$^1$H NMR (CDCl$_3$) δ: 5.30 (br s, 1H, NH), 4.25 (br s, 1H, H4), 3.72 (s, 3H, OCH$_3$), 3.37 (m, 1OH, H5), 3.40-3.05 (m, 4H, H5', Boc-NH—CH$_2$, OH), 2.65 (m, 3H, H2, Boc-NH—CH$_2$—CH$_2$), 2.40 (m, 1H, H3), 1.92 (dd, 1H, H3'), 1.40 (s, 9H, C(CH$_3$)$_3$).

$^{13}$C NMR (CDCl$_3$) δ: 174.9 (COOCH$_3$), 156.1 (COOC(CH$_3$)$_3$), 78.6 (C(CH$_3$)$_3$), 70.0 (OCH$_3$), 64.6 (C4), 61.6 (C5), 53.9 (C3), 51.9 (C2), 39.0 (Boc-NH—(CH$_2$)$_2$), 28.3 ((CH$_3$)$_3$).

EXAMPLE 5

[1-(N-Boc)-2-aminoethyl]-4(S)-(N3-benzoylthymin-1-yl)-2(S)-prolinemethylester 4a To a stirred solution of [1-(N-Boc)-2-aminoethyl]-4(R)-hydroxy-2(S)-prolinemethylester 3 (0.9 g, 3.2 mmol), N3-benzoylthymine (0.74 g, 3.2 mmol) and triphenyl phosphine (1 g, 3.8 mmol) in dry THF (10 ml) at room temperature, was added dropwise diisopropylazodicarboxylate (DIAD, 0.76 ml, 3.8 mmol). After completion of the reaction as indicated by TLC (24 h), the solvent was removed in vacuo and residue purified by silica gel column chromatography to get the pure product (0.6 g, 38%).

$^1$H NMR (CDCl$_3$) δ: 8.10 (s, 1H, T-H6), 7.90 (d, 2H, Bz, o-CH), 7.65 (t, 1H, Bz-p-CH), 7.50 (t, 2H, Bz, m-CH), 5.25 (m, 2H, Boc-NH, H4), 3.80 (s, 3H, OCH$_3$), 3.25 (m, 4H, Boc-NH—CH$_2$, H5, H5'), 2.80 (m, 3H, Boc-NH—CH$_2$—CH$_2$, H2), 2.60 (m, 1H, H3), 2.00 (s, 3H, T-CH$_3$), 1.95 (m, 1H, H3'), 1.45 (s, 9H, (CH$_3$)$_3$)

EXAMPLE 6

[1-(N-Boc)-2-aminoethyl]-4(S)-(N3-benzoylthymin-1-yl)-2(R)-prolinemethylester 6a To a stirred solution of 1-(N-Boc-aminoethyl)-4(R)-hydroxy-2(R)-prolinemethylester 5 (0.9 g, 3.2 mmol), N3-benzoylthymine (0.74 g, 3.2 mmol) and triphenyl phosphine (1 g, 3.8 mmol) in dry THF (10 ml) at room temperature, was added dropwise diisopropylazodicarboxylate (DIAD, 0.76 ml, 3.8 mmol). After completion of the reaction as indicated by TLC (24 h), the solvent was removed in vacuo and residue purified by silica gel column chromatography to get the pure product (0.47 g, 30%).

¹H NMR (CDCl₃) δ: 7.92 (d, 2H, Bz-o-CH), 7.65 (t, 1H, Bz-p-CH), 7.50 (t, 2H, Bz-m-CH), 7.40 (s, 1H, T-H6), 5.25 (m. 1H, H4), 4.90 (br t, 1H, Boc-NH), 3.90 (dd, 1H, H5), 3.72 (s, 3H, OCH₃), 3.30 (m, 3H, H5', Boc-NH—CH₂), 2.92 (dd, 1H, H2), 2.78 (t, 2H, Boc-NH—CH₂—CH₂), 2.55 (m, 1H, H3), 2.20 (m, 1H, H3'), 2.00 (s, 3H, T-CH₃), 1.45 (s, 9H, C(CH₃)₃)

¹³C NMR (CDCl₃) δ: 172.5 (COOCH₃), 169.0 (COOC(CH₃)₃), 162.5 (T-C2), 155.8 (Ph-CO), 149.5 (T-C4), 137.5 (T-C6), 134.8, 131.3, 130.0 & 128.9 (Ph), 111.1 (T-C5), 78.8 (C(CH₃)₃), 63.1 (C4), 55.5 (Boc-NH—CH₂), 53.7 (C2), 51.4 (OCH₃), 50.6 (C5), 38.7 (Boc-NH—CH₂CH₂), 35.1 (C3), 28.1 (C(CH₃)₃), 12.3 (T-CH₃)

EXAMPLE 7

Solid Phase Synthesis, Deprotection and Purification of the Oligomers 7-13 (FIG. 8) of the Invention The oligomers of the invention were synthesized on Merrifeld resin (100 mg, pre swollen in dichloromethane) derivatized with β-alanine as a spacer chain (0.13 meq/g of resin). Solid phase synthesis was carried out employing the well known Boc protection strategy involving successive cycles of (i) Boc deprotection using TFA-DCM (1:1, 2 mL, 20 min), (ii) neutralization of the resulting TFA salt by washing with 5% DIPEA in DCM, (2 mL, 5 min) (iii) coupling of the desired aep/aegPNA monomer in DMF using HOBT and diisopropylcarbodiimide as the coupling agents (2-5 h). At the end, the oligomers were cleaved from the solid support by TFMSA/TFA to obtain oligomers with β-alanine as a free carboxylic acid at C-terminus. The oligomers 7-13 were purified initially by gel filtration over Sephadex G25 and later by reverse phase FPLC on a C-8 column, eluting with an ascending gradient of water-acetonitrile containing 0.1% TFA. The purity was checked by reverse phase HPLC on a C-18 column and molecular composition confirmed by MALDI-TOF mass spectrometric analysis.

EXAMPLE 8

DNA Hybridization Studies with the Oligomers of the Invention

The concentration of oligonucleotides (14-16, FIG. 8) and oligomers of the invention were determined from the absorbance at 260 nm, using the molar extinction coefficients, of A, 15.4 cm²/μmol; T 8.8 cm²/μmol, G, 11.7 cm²/μmol, C, 7.3 cm²/μmol. All Tm measurements were carried out on Perkin-Elmer Lambda UV spectrometer equipped with a multiple cell holder and variable temperature accessory. A programmable Julabo water circulator controlled the temperature. The samples were prepared by mixing calculated amounts of stock oligonucleotide and the oligomer of the invention together with the addition of calculated amounts of NaCl and sodium phosphate, pH 7.0. to a final volume of 2 mL in a sample cuvette. The samples were annealed by heating at 85° C. for 5 min, followed by slow cooling to 5° C. The $OD_{260}$ was then recorded in steps from 10-85° C., with a temperature increment of 0.5° C./min. The results were plotted as percent hyperchromicity at 260 nm as a function of temperature. Analyses of the data were performed by using Microcal Origin software. The melting temperatures were determined from the midpoints of the percent hyperchromicity at 260 nm Vs temperature plots.

EXAMPLE 9

Gel Electrophoretic Experiments

The samples were prepared by mixing stock solutions of the oligomers of the invention and oligonucleotides in tris-EDTA buffer, pH 7.0. These were annealed by heating at 85° C. for 5 min., followed by slow cooling to 10° C. The samples were subjected to gel electrophoresis using 15% PAGE (acrylamide:bisacrylamide, 29:1) gels of 1 mm thick and 15 cm long Electrophoresis were carried out at a constant voltage of 150 V till the marker bromophenol dye migrated to 12 cm length on the gel. The bands were visualized by illuminating the gel (254 nm) after placing it on a fluorescent thin-layer silica gel chromatographic plate.

The invention claimed is:

1. A compound having the formula

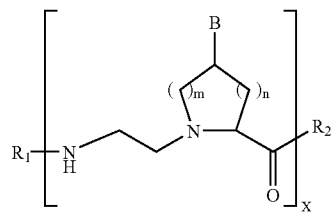

aep PNA II wherein m and n are 1 to 2 and x=1-20;

each of B is independently selected from the group consisting of naturally occurring nucleobases adenine (A), thymine (T), cytosine (C) and guanine (G), and non-naturally occurring nucleobases;

each chiral monomeric unit is independently selected from the four possible diastereomers; and $R_1$=H or Fluorophore or Biotin, $R_2$=OH or $NH(CH_2)_2COOH$ or $NH(CH_2)_3NH(CH_2)_4NH(CH_2)_3NH_2$.

2. A compound having the formula

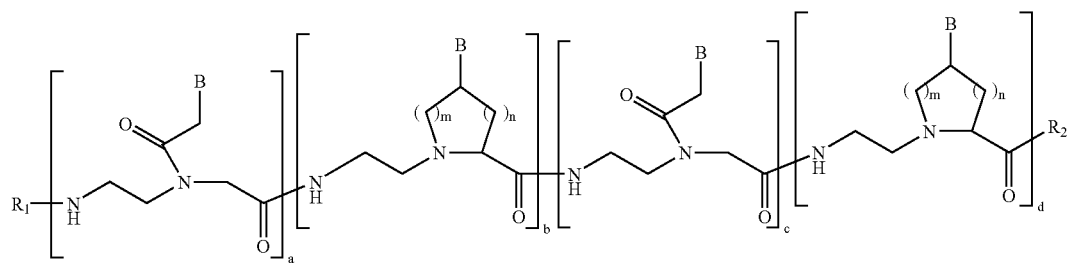

aep PNA III that is heteropolymeric aepPNA III comprising non-chiral aeg unit of aminoethylglycyl PNA I and chiral aep monomeric unit IV

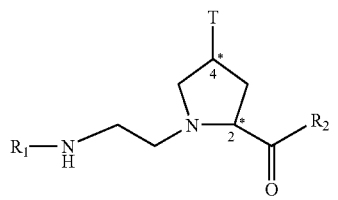

wherein
T is a nucleobase;
each chiral monomer unit is independently selected from the four possible diastereomers;
a, b, c, d, m, n are integers with independent values in the range 1 to 10;
$R_1$ is H, $COCH_3$ or L (L=dansyl, carboxyfluoresceinyl);
$R_2$ is OH, $NH_2$, $NHCH_2CH_2COOH$, or $NH(CH_2)_3NH(CH_2)_4NH(CH_2)_3NH_2$, and
each of B is independently selected from the group consisting of H, HO, $NH_2$, naturally occurring nucleobases, non-naturally occurring nucleobases, DNA intercalators, heterocyclic moieties and reporter ligands.

3. The compound as claimed in claim 2, wherein
 i) m=n=1, B=T, $R_1$=H, $R_2$=$NH(CH_2CH_2)COOH$, a=7, b=1, c=d=0;
 ii) m=n=1, B=T, $R_1$=H, $R_2$=$NH(CH_2CH_2)COOH$, a=c=3, b=d=1;
 iii) m=n=1, B=T, $R_1$=H, $R_2$=$NH(CH_2CH_2)COOH$, a=b=c=d=1, and wherein chiral monomeric units a, b, c, and d occur twice in that order;
 iv) m=n=1, B=T, $R_1$=H, $R_2$=$NH(CH_2CH_2)COOH$, a=b=c=0, d=8; and
 v) m=n=1, B=T, $R_1$=H, $R_2$=$NH(CH_2CH_2)COOH$, a=d=0, b=1, c=7.

4. The compound as claimed in claim 2, wherein said compound is synthesized by adaptation of standard solution phase peptide synthesis procedures or standard solid phase peptide synthesis procedures.

5. The compound as claimed in claim 3, wherein said compound is synthesized by adaptation of standard solution phase peptide synthesis procedures or standard solid phase peptide synthesis procedures.

6. A monomer precursor-synthon of formula IV

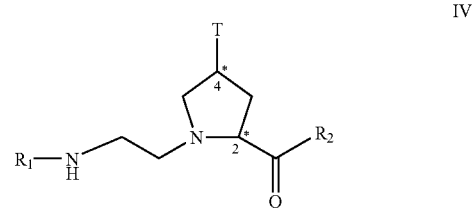

wherein
$R_1$=H, Boc or Fmoc:
$R_2$=OMe, H, OEt or OBenzyl;
chirality at positions 2 and 4 results in four diastereomers (2S,4R), (2R,4S), (2S,4S) and (2R,4R); and
T is a nucleobase.

7. The monomer precursor-synthon as claimed in claim 6 wherein T is a naturally occurring nucleobase.

8. A pharmaceutical composition comprising a compound according to claim 1, along with any other pharmaceutically effective agent.

9. A pharmaceutical composition comprising a compound according to claim 2, along with any other pharmaceutically effective agent.

10. A process for preparing compounds of formulae 4a and 6a

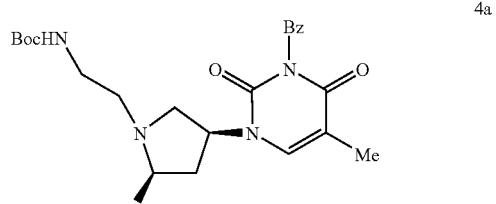

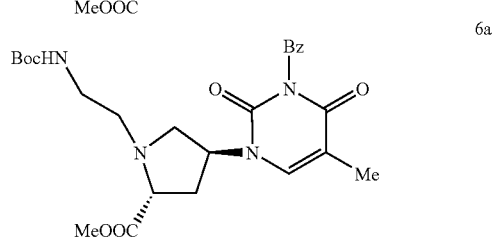

comprising the steps of
- A. a) synthesizing (N-Boc)-2-aminoethanol from 2-aminoethanol;
  - b) synthesizing (N-Boc)-2-aminoethylbromide from (N-Boc)-2-aminoethanol;
- B. N-alkylation of 4-hydroxyprolinemethylester with (N-Boc)-2-aminoethanol prepared as in step A;
  - (i) alkylation of 4R-hydroxy-2S-prolinemethylester with (N-Boc)-2-aminoethylbromide to obtain 1-(N-Boc-aminoethyl)-4R-hydroxy-2S-prolinemethyl ester;
  - (ii) alkylation of 4R-hydroxy-2R-prolinemethylester with (N-Boc)-2-aminoethyl bromide to obtain 1-(N-Boc-aminoethyl)-4R-hydroxy-2R-prolinemethyl ester;
  - (iii) alkylation of 4S-hydroxy-2R-prolinemethylester with (N-Boc)-2-aminoethyl bromide to obtain 1-(N-Boc-aminoethyl)-4S-hydroxy-2R-prolinemethylester;
  - (iv) alkylation of 4S-hydroxy-2S-prolinemethylester with (N-Boc)-2-aminoethyl bromide to obtain —(N-Boc-aminoethyl)-4S-hydroxy-2S-prolinemethylester;
- C. Mitsunobu reaction of compounds 1-(N-Boc-aminoethyl)-4R-hydroxy-2S-prolinemethyl ester and (N-Boc)-2-aminoethanol prepared according to steps B(i) and B(ii) with N3-benzoylthymine, to produce monomer synthons of formulae 4a and 6a, respectively.

* * * * *

SEQUENCE LISTING

```
<160> NUMBER OF SEQ ID NOS: 5

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: aepPNA-t
<220> FEATURE:
<223> OTHER INFORMATION: peptide nucleic acid oligomer

<400> SEQUENCE: 1
```

-continued

```
tatattatta tt                                                         12

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: peptide nucleic acid oligomer

<400> SEQUENCE: 2
tatattatta tt                                                         12

<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcaaaaaaaa cg                                                         12

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcaaataaaa cg                                                         12

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aataataata ta                                                         12
```